United States Patent [19]

Henkel et al.

[11] 4,279,891

[45] Jul. 21, 1981

[54] LOW ALCOHOL CONTENT AFTER-SHAVE LOTION

[75] Inventors: Herbert W. Henkel, East Hanover; Mary R. Paradiso, Clifton, both of N.J.

[73] Assignee: American Cyanamid Company, Stamford, Conn.

[21] Appl. No.: 102,724

[22] Filed: Dec. 13, 1979

Related U.S. Application Data

[63] Continuation of Ser. No. 10,198, Feb. 8, 1979, abandoned, which is a continuation of Ser. No. 863,564, Dec. 22, 1977, abandoned.

[51] Int. Cl.³ .......................... A61K 7/15; A61K 7/42
[52] U.S. Cl. .......................................... 424/73; 424/59; 424/316; 424/343
[58] Field of Search .................................. 424/73, 316

[56] References Cited

U.S. PATENT DOCUMENTS

| | | | |
|---|---|---|---|
| 3,328,307 | 6/1967 | Schmitz | 424/316 |
| 3,912,662 | 10/1975 | Martinsson et al. | 252/DIG. 7 X |
| 3,928,251 | 12/1975 | Bolich, Jr. et al. | 252/DIG. 7 X |

FOREIGN PATENT DOCUMENTS 1209367 10/1970 United Kingdom ..................... 252/522

*Primary Examiner*—Dale R. Ore
*Attorney, Agent, or Firm*—Charles J. Fickey

[57] ABSTRACT

A clear, aqueous, alcoholic after-shave lotion having low alcohol content and therefore having reduced skin sting thereby being more compatible with a more sensitive skin.

4 Claims, No Drawings

LOW ALCOHOL CONTENT AFTER-SHAVE LOTION

This is a continuation of application Ser. No. 10,198, filed Feb. 8, 1979, now abandoned which is a continuation of Ser. No. 863,564, filed Dec. 22, 1977, now abandoned.

The present invention relates to clear, aqueous, alcoholic after-shave lotions which are characterized by low-alcohol content, reduced skin sting, and unique after-feel. More particularly, the invention relates to clear, perfumed, aqueous, alcoholic after-shave lotion compositions whereby the insoluble perfume is solubilized by use of an ethoxylated fatty alcohol and an amphoteric betaine surfactant in certain proportions which are defined below. Moreover, the invention relates to a composition comprising an ethoxylated fatty alcohol and an amphoteric betaine for solubilizing a perfume compound in aqueous alcohol.

The solubilization of perfumes in water and aqueous systems using surfactants and other chemicals has been known for many years. However, this is normally accomplished using levels of solubilizing agents many times larger than the level of perfume used in the finished composition, for example, about 4 to 6 times the level. Moreover, most, if not all, clear after-shave lotions use an alcohol content of greater than 50 percent by weight in order to solubilize the perfumes. The high alcohol content produces a sting or burning sensation to the skin when applied following shaving.

The present invention provides an after-shave lotion characterized as a clear, aqueous, alcoholic composition which is non-viscous, non-oily, and non-greasy and which has significantly low skin sting and unique after-feel when applied to the face following shaving.

The compositions of the invention consist essentially of a clear solution of alcohol, water, and a perfume compound which is solubilized using a combination of an amphoteric betaine surfactant and an ethoxylated fatty alcohol.

In accordance with the invention, compositions are provided which consist essentially of from about 0.25 to 3.75 percent by weight of a water insoluble perfume compound, at least about 66 percent by weight of water, not more than about 20 percent by weight of ethanol, an amphoteric betaine surfactant, and an ethoxylated fatty alcohol; the composition being characterized as having a ratio of perfume to amphoteric betaine surfactant of from about 2/1 to 4.6/1 and a ratio of perfume to ethoxylated fatty alcohol of about 1/1 to 3/1.

The amphoteric betaine surfactant generally conforms to one of Formulas (A) or (B):

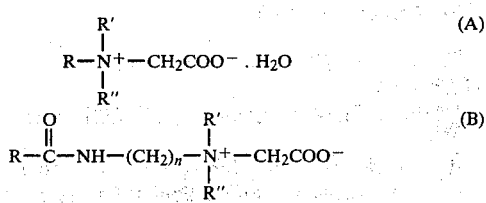

wherein R represents a saturated or unsaturated $C_{12}$ to $C_{18}$ alkyl group; R' and R'' represent a $C_1$-$C_4$ alkyl group; and n is an integer from 1 to 6. The amphoteric betaines represented by Formula (A) are preferred. Examples of suitable amphoteric betaines include:

(carboxymetyl) lauryl dimethyl ammonium hydroxide
(carboxymethyl) lauryl diethyl ammonium hydroxide
(carboxymethyl) lauryl dibutyl ammonium hydroxide
(carboxymethyl) myristyl dimethyl ammonium hydroxide
(carboxymethyl) cetyl dimethyl ammonium hydroxide
(carboxymethyl) cetyl diethyl ammonium hydroxide
(carboxymethyl) stearyl dimethyl ammonium hydroxide
(carboxymethyl) stearyl diethyl ammonium hydroxide
(carboxymethyl) eicosyl dimethyl ammonium hydroxide
(carboxymethyl) oleyl dimethyl ammonium hydroxide
(carboxymethyl) coco dimethyl ammonium hydroxide
(carboxymethyl) linoleyl dimethyl ammonium hydroxide
lauramidopropyl dimethyl glycine
lauramidomethyl dimethyl glycine
cetylamidopropyl dimethyl glycine
stearamidopropyl diethyl glycine
stearamidopropyl dibutyl glycine
cocamidopropyl dimethyl glycine, and the like.

The ethoxylated fatty alcohol is generally represented by the following structure:

$$R\text{-}(OCH_2CH_2)_n\text{-}OH$$

wherein R represents a saturated or unsaturated $C_{12}$ to $C_{18}$ alkyl group and n has an average value of about 10 to 20, preferably about 10 to 13. The ethoxylated fatty alcohol is a solubilizer for the perfume compound and, in addition, imparts emolliency, lubricity and slip to the skin.

Representative ethoxylated fatty alcohols include:
lauryl alcohol ethoxylated with an average of 10 moles of ethylene oxide
lauryl alcohol ethoxylated with an average of 12 moles of ethylene oxide
lauryl alcohol ethoxylated with an average of 20 moles of ethylene oxide
myristyl alcohol ethoxylated with an average of 10 moles of ethylene oxide
cetyl alcohol ethoxylated with an average of 12 moles of ethylene oxide
cetyl alcohol ethoxylated with an average of 20 moles of ethylene oxide
stearyl alcohol ethoxylated with an average of 10 moles of ethylene oxide
stearyl alcohol ethoxylated with an average of 12 moles of ethylene oxide
stearyl alcohol ethoxylated with an average of 20 moles of ethylene oxide
eicosyl alcohol ethoxylated with an average of 12 moles of ethylene oxide
oleyl alcohol ethoxylated with an average of 10 moles of ethylene oxide, and the like.

The amphoteric betaine is also a solubilizer for the perfume compound. The betaine helps to maintain the clarity of the product and also is a mild surfactant and conditioning agent, which leaves the skin feeling smooth.

The ethoxylated fatty alcohol and the amphoteric betaine may be prepared as a mixture which is useful in solubilizing the perfume compound in aqueous alcohol solutions. The solubilizer composition may contain from about 45 to 90% by weight of ethoxylated fatty alcohol and from about 55 to 10% by weight, respectively, of amphoteric betaine. The preferred compositions will contain about equal weight proportions of each component.

Propylene glycol is added to the composition as an emollient to soften the skin. It may be present in amounts ranging from about 2 to 8 percent by weight, preferably 4 to 5 percent by weight.

The amount of water used in the after-shave should be greater than about 66 percent, and, preferably, will range from about 66 to 76 percent by weight. On the other hand, the alcohol content should be from about 15 to 20 percent by weight.

In addition to the aforementioned essential ingredients, any suitable preservative may be added, if needed, to prevent contamination by microorganisms. Also, UV absorbers may be added to prevent UV degradation of the perfume compound. Benzyl alcohol, which is a mild anti-irritant or anesthetic for the skin, may be added to the perfume compound, if desired.

EXAMPLE 1

A clear, after-shave lotion is prepared from the following composition (percentages by weight):

| | |
|---|---|
| Denatured alcohol (anhydrous) | 18.740 |
| Ethoxylated fatty alcohol* | 1.000 |
| Deionized water | 72.704 |
| Propylene glycol (USP) | 5.000 |
| Perfume compound | 2.100 |
| Betaine surfactant** (100%) | 0.456 |
| | 100.000 |

*Ethoxylated oleyl alcohol: less than 13 moles ethylene oxide per mole of oleyl alcohol
**(carboxymethyl) Cocodimethyl ammonium hydroxide In the above composition, the ratio of perfume compound: ethoxylated fatty alcohol=2.1; the ratio of perfume compound: betaine=4.6.

EXAMPLE 2

A clear, after-shave lotion is prepared from the following composition:

| | % |
|---|---|
| Denatured alcohol (anhydrous) | 19.04 |
| Deionized water | 70.02 |
| Perfume compound | 3.75 |
| Propylene glycol (USP) | 5.00 |
| Ethoxylated fatty alcohol* | 1.25 |
| Betaine surfactant** (100%) | 0.94 |
| | 100.00 |

*Lauryl alcohol ethoxylated with an average of about 10 moles of ethylene oxide
**(carboxymethyl) Cocodiethyl ammonium hydroxide Ratio perfume compound: ethoxylated fatty alcohol=3.0
Ratio perfume compound: betaine=4.0

EXAMPLE 3

A clear, after-shave lotion is prepared from the following composition:

| | % |
|---|---|
| Denatured alcohol (anhydrous) | 15.00 |
| Deionized water | 74.85 |
| Perfume compound | 2.10 |
| Propylene glycol (USP) | 6.00 |
| Ethoxylated fatty alcohol* | 1.00 |
| Betaine surfactant** (100%) | 1.05 |
| | 100.00 |

*Stearyl alcohol ethoxylated with an average of about 10 moles of ethylene oxide
**(carboxymethyl) Lauryl dimethyl ammonium hydroxide Ratio perfume compound: ethoxylated fatty alcohol=2.1
Ratio perfume compound: betaine=2.0

EXAMPLES 4–10

Using the ethoxylated fatty alcohol and amphoteric betaine of Example 1, the following after-shave lotion compositions are prepared:

| | 4 | 5 | 6 | 7 | 8 | 9 | 10 |
|---|---|---|---|---|---|---|---|
| Denatured alcohol (anhydrous) | 18.537 | 18.500 | 19.62 | 19.62 | 19.04 | 19.04 | 19.62 |
| Water | 75.838 | 75.937 | 66.00 | 67.87 | 67.52 | 69.39 | 68.50 |
| Perfume compound | 0.250 | 0.250 | 3.75 | 3.75 | 3.75 | 3.75 | 3.75 |
| Propylene glycol (USP) | 5.000 | 5.000 | 5.00 | 5.00 | 5.00 | 5.00 | 5.00 |
| Ethoxylated fatty alcohol | 0.250 | 0.250 | 3.75 | 1.88 | 3.75 | 1.88 | 1.25 |
| Amphoteric coco betaine | 0.125 | 0.063 | 1.88 | 1.88 | 0.94 | 0.94 | 1.88 |
| | 100.000 | 100.000 | 100.00 | 100.00 | 100.00 | 100.00 | 100.00 |
| Ratio: Perfume compound / Ethoxylated fatty alcohol | 1:1 | 1:1 | 1:1 | 2:1 | 1:1 | 2:1 | 3:1 |
| Ratio: Perfume compound / Amphoteric betaine | 2:1 | 4:1 | 2:1 | 2:1 | 4:1 | 4:1 | 2:1 |

EXAMPLE 11

A clear, after-shave lotion is prepared from the following composition (percentages by weight):

| | % |
|---|---|
| Denatured alcohol (anhydrous) | 18.46 |
| Water | 72.39 |
| Perfume compound | 2.10 |
| Propylene glycol (USP) | 5.00 |
| Ethoxylated fatty alcohol* | 1.00 |
| Amphoteric betaine** | 1.05 |
| | 100.00 |

*Ethoxylated oleyl alcohol; less than 13 moles of ethylene oxide per mole of oleyl alcohol
**Cocamidopropyl dimethyl glycine Ratio perfume compound: ethoxylated fatty alcohol=2.1
Ratio perfume compound: amphoteric betaine=2.0

We claim:
1. A clear, non-oily, non-greasy, low-sting aqueous alcoholic after-shave lotion consisting essentially of at least about 66 percent by weight water and from about 15 to 20 percent by weight ethanol; from about 0.25 to 3.75 percent by weight of a perfume compound which is insoluble in said aqueous alcohol solution; and from about 2 to 8 percent by weight of propylene glycol; and, as a solubilizer for said perfume compound (A), an amphoteric betaine surfactant selected from the group consisting of compounds represented by (I) and (II):

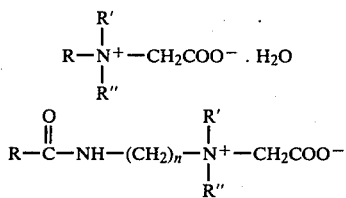

wherein R is a saturated or unsaturated $C_{12}$ to $C_{18}$ alkyl group; R' and R" are $C_1$ to $C_4$ alkyl groups; n is an integer from 1 to 6; and (B) an ethoxylated fatty alcohol represented by (III):

wherein R''' represents a saturated or unsaturated $C_{12}$ to $C_{18}$ alkyl group and n has an average value of about 10 to 20; the weight ratio of said perfume compound to said amphoteric betaine in said lotion being from about 2/1 to 4.6/1, and the weight ratio of said perfume compound to said ethoxylated fatty acid being from about 1/1 to 3/1.

2. An after-shave lotion in accordance with claim 1 wherein said amphoteric betaine is (carboxymethyl) coco dimethyl ammonium hydroxide.

3. An after-shave lotion in accordance with claim 1 wherein said ethoxylated fatty alcohol has a value of n of from about 10 to 13.

4. An after-shave lotion in accordance with claim 3 wherein said ethoxylated fatty alcohol is ethoxylated oleyl alcohol.

* * * * *